(12) United States Patent
Umbach

(10) Patent No.: US 11,628,080 B2
(45) Date of Patent: Apr. 18, 2023

(54) POST GASTRECTOMY ANCHORING PROCEDURE

(71) Applicant: Thomas Umbach, Las Vegas, NV (US)

(72) Inventor: Thomas Umbach, Las Vegas, NV (US)

( * ) Notice: Subject to any disclaimer, the term of this patent is extended or adjusted under 35 U.S.C. 154(b) by 356 days.

(21) Appl. No.: 17/117,019

(22) Filed: Dec. 9, 2020

(65) Prior Publication Data

US 2022/0175566 A1 Jun. 9, 2022

(51) Int. Cl.
*A61F 5/00* (2006.01)
*A61B 17/00* (2006.01)

(52) U.S. Cl.
CPC .......... *A61F 5/0063* (2013.01); *A61F 5/0083* (2013.01); *A61B 2017/00818* (2013.01)

(58) Field of Classification Search
CPC .................. A61F 5/0076; A61F 5/0083; A61F 2002/045; A61B 17/1114; A61B 2017/00818; A61B 2017/00827
See application file for complete search history.

(56) References Cited

PUBLICATIONS

Santoro S, Lacombe A, Aquino CG, Malzoni CE. Sleeve gastrectomy with anti-reflux procedures. Einstein (Sao Paulo). Sep. 2014;12(3):287-94 (Year: 2014).*
Elbalshy, Mohammed & Fayed, Asem & Abdelshahid, Moharam & Alkhateep, Yahia. (2017). Role of staple line fixation during laparoscopic sleeve gastrectomy. International Surgery Journal. 5(1): 156-161 (Year: 2017).*
Tirkes T, Sandrasegaran K, Patel AA, Hollar MA, Tejada JG, Tann M, Akisik FM, Lappas JC. Peritoneal and retroperitoneal anatomy and its relevance for cross-sectional imaging. Radiographics. Mar.-Apr. 2012;32(2):437-51. (Year: 2012).*
Acquafresca PA, Palermo M, Rogula T, Duza GE, Serra E. Most common robotic bariatric procedures: review and technical aspects. Ann Surg Innov Res. Oct. 28, 2015;9:9. (Year: 2015).*
Daes J, Jimenez ME, Said N, Daza JC, Dennis R. Laparoscopic sleeve gastrectomy: symptoms of gastroesophageal reflux can be reduced by changes in surgical technique. Obes Surg. Dec. 2012;22(12):1874-9. (Year: 2012).*

* cited by examiner

*Primary Examiner* — Catherine B Kuhlman
(74) *Attorney, Agent, or Firm* — Lightbulb IP, LLC

(57) ABSTRACT

A post gastrectomy anchoring procedure comprises anchoring a sleeve created by a gastrectomy to tissue structure that can better immobilize the sleeve to reduce complications relating to mobility of the sleeve. Namely, the anchoring procedure secures one or more portions of the sleeve to retroperitoneal fat of a patient. One or more bindings attach the sleeve to the retroperitoneal fat. The bindings can be installed to hold the sleeve in a bent or other shape, such as to mimic the natural shape of the patient's stomach and maintain an opening in the angularis of the sleeve.

20 Claims, 3 Drawing Sheets

POST GASTRECTOMY ANCHORING PROCEDURE

BACKGROUND OF THE INVENTION

1. Field of the Invention

The invention relates to supports for bariatric treatments and in particular to a post gastrectomy anchoring procedure.

2. Related Art

Bariatric treatments may be used to treat obesity or other weight problems by reducing the size of a patient's stomach. The patient then consumes smaller portions of food leading to weight loss. Traditional bariatric treatments include gastric bypass surgery, gastric band surgery, gastric plication, sleeve gastrectomy, and placement of an intragastric balloon.

From the discussion that follows, it will become apparent that the present invention addresses the deficiencies associated with the prior art while providing numerous additional advantages and benefits not contemplated or possible with prior art constructions.

SUMMARY OF THE INVENTION

A post gastrectomy anchoring procedure for reducing mobility-related complications is disclosed herein. As will be described further below, the anchoring procedure is advantageous in that it provides improved immobility for a sleeve without the need for excessive binding of the sleeve to secure the sleeve in place. This reduces post gastrectomy mobility-related complications.

In addition, the reduction in the quantity of bindings avoids damage caused by some traditional methods of immobilizing a sleeve as well as the risks involved with the same. The duration of gastrectomies performed with the anchoring procedure herein is also reduced by the reduction in bindings.

Various systems and methods for the anchoring procedure are disclosed herein. For instance, in one exemplary embodiment, a method for a gastrectomy is disclosed. Such method comprises dividing a stomach to form a sleeve, accessing one or more portions of retroperitoneal fat, and anchoring one or more portions of the sleeve to the portions of the retroperitoneal fat with one or more bindings. It is noted that, the bindings may number no more than three bindings.

The portions of retroperitoneal fat may be accessed through one or more portions of mesenteric fat. Accessing the portions of the retroperitoneal fat may comprise making an incision in one or more portions of mesenteric fat.

The portions of the sleeve may be positioned adjacent or in engagement with the portions of the retroperitoneal fat prior to anchoring the portions of the sleeve. The portions of the sleeve may be anchored such that an opening at an angularis of the sleeve is maintained.

In another exemplary embodiment, a method for post gastrectomy anchoring of a sleeve created during a gastrectomy is disclosed. Such method comprises accessing one or more portions of retroperitoneal fat, positioning one or more portions of the retroperitoneal fat adjacent the sleeve, and anchoring the portions of the retroperitoneal fat to one or more portions of the sleeve with one or more bindings. The retroperitoneal fat is accessed through one or more portions of mesenteric fat.

The bindings may be installed at the greater curve of the sleeve. Similar to above, the bindings may number no more than three bindings. The portions of the sleeve may be anchored such that an opening at an angularis of the sleeve is maintained. In addition, the portions of the sleeve may be anchored to hold the sleeve in a bent shape.

Accessing the portions of the retroperitoneal fat may include making an incision in one or more portions of mesenteric fat. The portions of the retroperitoneal fat may be placed in engagement with the portions of the sleeve prior to anchoring.

In another exemplary embodiment, a method for reducing post gastrectomy complications is disclosed. Such method comprises positioning one or more portions of a sleeve created during a gastrectomy relative to retroperitoneal fat and anchoring the portions of the sleeve to the retroperitoneal fat with one or more bindings. The bindings extend through one or more portions of mesenteric fat when anchoring the portions of the sleeve to the retroperitoneal fat. The bindings may number no more than two or three bindings.

In addition, the portions of the sleeve may be anchored such that an opening at an angularis of the sleeve is maintained. The portions of the sleeve may be anchored to hold the sleeve in a bent shape. The bindings may be installed at the greater curve of the sleeve.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION OF THE INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

Figure 1:
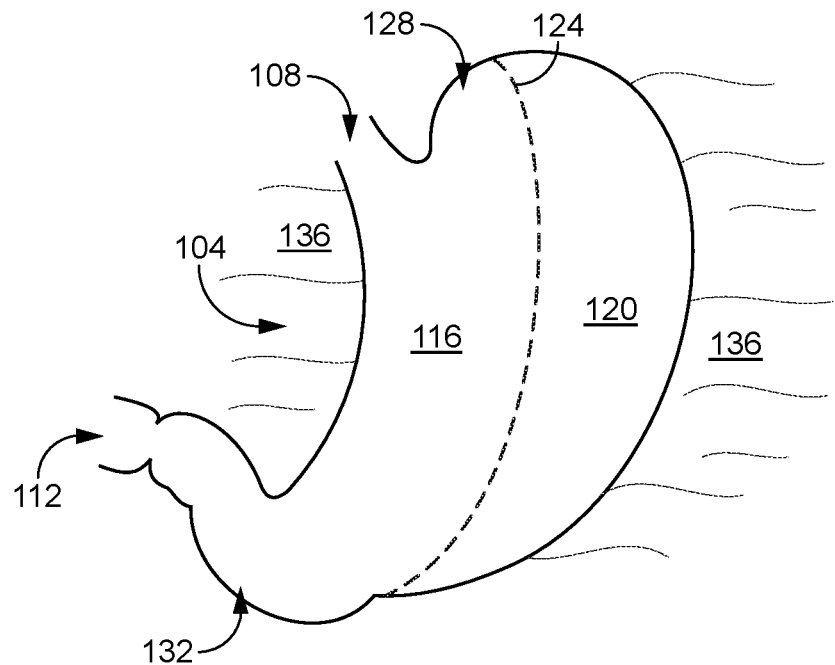
FIG. 1 is an anterior view of an exemplary stomach region of a patient.
Figure 2:
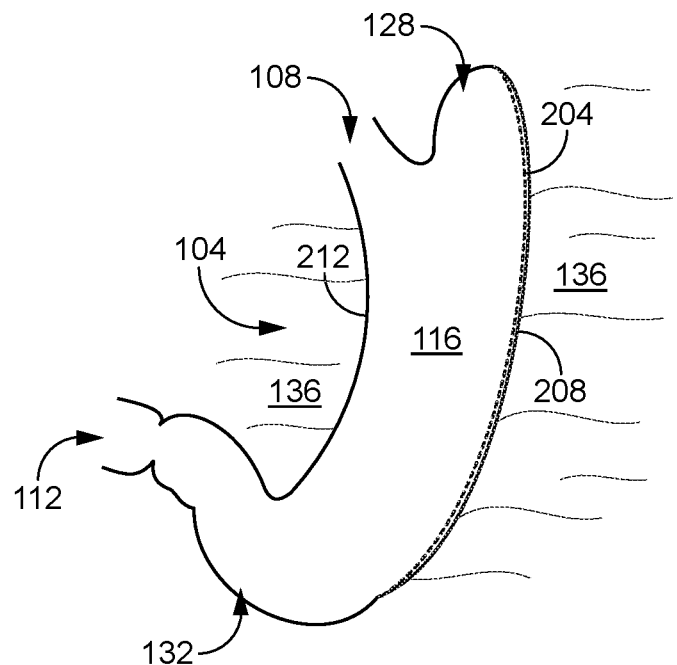
FIG. 2 is an anterior view of an exemplary sleeve.

In general, a gastrectomy reduces the volume of a patient's stomach 104 thereby reducing the patient's appetite to induce weight loss. FIGS. 1 and 2 respectively illustrate a stomach 104 before and after a gastrectomy.

As will be described further below, the invention herein addresses mobility of the stomach 104 after a gastrectomy, which can occur in as many as two out of 100 patients. Such mobility can cause significant pain and discomfort as well as herniation of the stomach 104, thereby requiring a patient to undergo another surgical procedure to repair and immobilize the area.

As can be seen, the stomach 104 may be divided first by fusing or otherwise binding a length 124 of the stomach 104 together to form a sleeve 116 and a sectioned portion 120. The sectioned portion will subsequently be removed from the patient.

The sleeve 116 forms a new stomach 104 with a reduced volume. As shown in FIG. 2, the stomach 104 has been stapled with a plurality of staples 204 to form a sleeve 116 of reduced volume as well as a new greater curve 208. The lesser curve 212 is maintained. Though described as fused via staples 204, it will be understood that various other tissue fusing or binding techniques and implements may be used.

Subsequent the procedure, a fundus 128 remains at the stomach's top end and a pylorus 132 remains at the bottom end of the sleeve 116. The cardial sphincter 108 connects the stomach 104 to the esophagus and allows ingested material to enter the reduced volume stomach 104 formed by the sleeve 116. After digestion in the sleeve 116, the ingested material can subsequently pass through the pyloric sphincter 112 to the small intestines to continue digestion.

Traditionally, a sleeve 116 is immobilized by binding the sleeve to adjacent mesenteric fat 136, such as with a single suture. Fewer sutures are desirable in that damage to tissues for each additional suture is avoided. However, a low number of sutures can be insufficient to immobilize a sleeve 116, leading to the complications, including herniation, as described above.

A traditional alternative is to bind the sleeve 116 to adjacent mesenteric fat 136 by suturing along the length of the sleeve 116, such as along the greater curve 208. As alluded to above however, this binding process causes an unnecessary amount of tissue damage by repeated punctures, manipulation, and other trauma of the sleeve 116 to accomplish the same. In addition, application of these additional sutures increases the risk of damage to other tissues and increases the duration of the surgical procedure for the patient.

The anchoring procedure disclosed herein is advantageous in that a sleeve 116 is better secured with a low number of sutures, staples, or other bindings. This immobilization provides the body time to "scar in" the sleeve 116, thereby naturally securing the sleeve, a process which can require a period of 3 to 4 weeks. This avoids the damage described above while also reducing the need for readmission, or even additional surgical procedures, to repair mobility related complications subsequent a gastrectomy.

Figure 3:
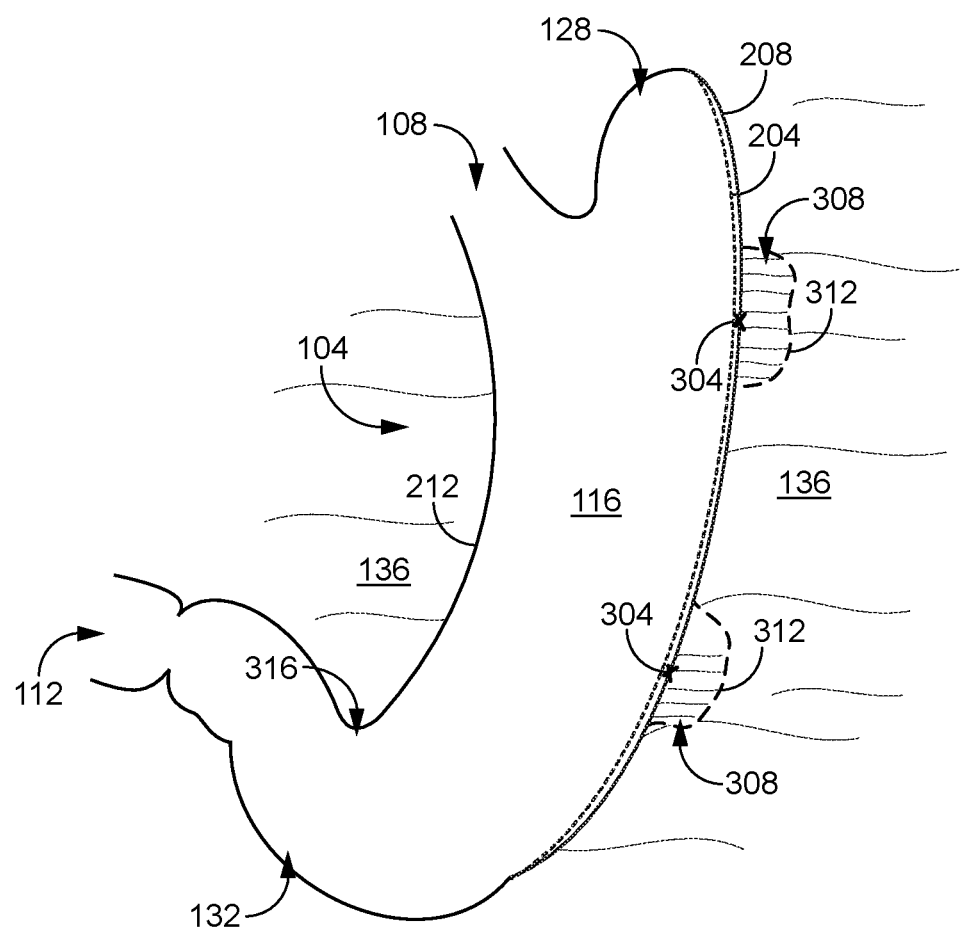
FIG. 3 is an anterior view of an exemplary anchored sleeve.

Referring to FIG. 3, it can be seen that the anchoring procedure immobilizes a sleeve 116 without the need for attachment to mesenteric fat 136. The anchoring procedure secures a sleeve 116 to retroperitoneal fat 308, which can be found below the mesenteric fat 136. The retroperitoneal fat 308 is typically structurally stronger that mesenteric fat 136, which provides for improved immobilization of a sleeve 116 attached thereto, even with a low number of bindings 304.

As can be seen, one or more bindings 304 may secure the sleeve 116 to retroperitoneal fat 308. One or more incisions 312 or other openings may be made to access the retroperitoneal fat 308, such as with a scalpel or other surgical implement, if necessary. Alternatively or in addition, a binding 304 may be placed or otherwise installed such that it passes through any interstitial tissues.

The portion of the sleeve 116 to be anchored may then be positioned adjacent the retroperitoneal fat 308. In one or more embodiments, the portion of the sleeve 116 may engage the retroperitoneal fat 308. A binding 304 may then be installed such that the binding attaches the sleeve 116 to retroperitoneal fat 308 thereby anchoring the sleeve.

Though shown with two bindings 304, it is contemplated that various numbers of bindings may be used with the anchoring process herein. As stated, a low number of bindings 304 will typically be used. Typically, for example, three or fewer bindings 304 may be used.

In addition, though shown as anchoring a sleeve 116 at its greater curve 208, it is contemplated that one or more bindings 304 may anchor other portions of a sleeve 116 to retroperitoneal fat 308. In addition, it is contemplated that one or more bindings 304 may be positioned to secure a bend or other shape for the sleeve 116, such as to mimic the natural or original shape of the patient's stomach. This is advantageous in that such shaping of the sleeve 116 may aid in keeping the angularis 316 open after a gastrectomy. In addition, it is contemplated that a sleeve 116 may be anchored such that it is held in a flatter or more "laid out" arrangement.

Figure 4:
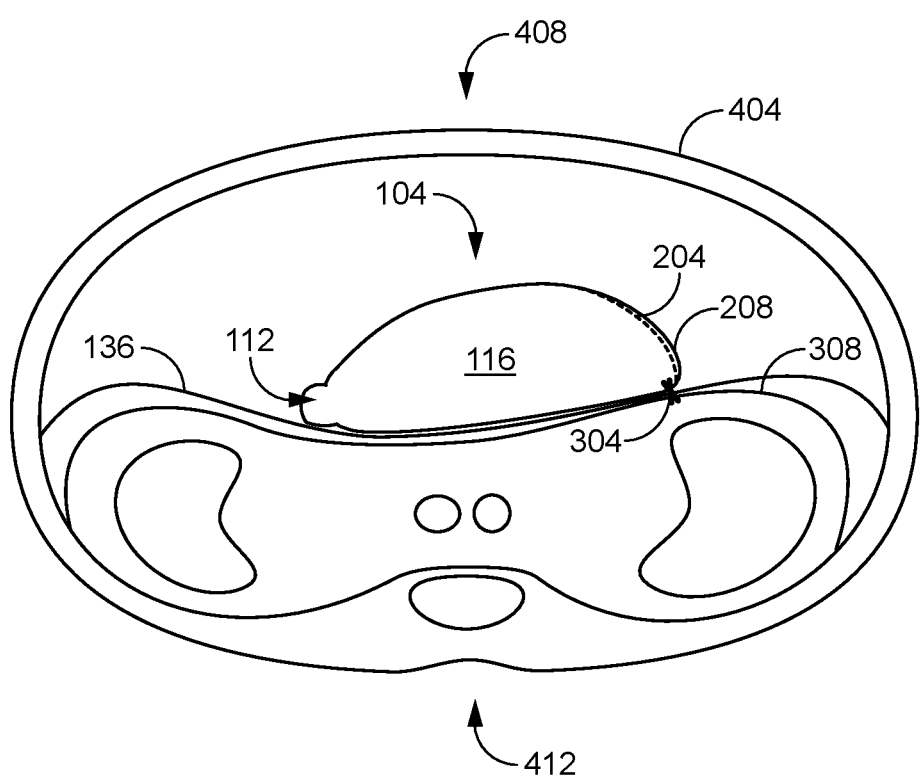
FIG. 4 is a cross sectional view of an exemplary anchored sleeve.

Referring to FIG. 4, which illustrates a cross-sectional view of a patient's torso 404 between the anterior 408 and posterior 412 thereof, it can be seen that retroperitoneal fat 308 is typically located behind mesenteric fat 136. In addition, it can be seen that one or more bindings 304 may anchor a sleeve 116 by extending from the sleeve to a portion of the retroperitoneal fat 308. As can also be seen, a binding 304 may pass through various tissues during placement. In FIG. 4 for instance, a binding 304 anchors the sleeve 116 to retroperitoneal fat 308 while passing through mesenteric fat 136.

Though described herein with respect to traditional gastrectomies, it will be understood that the anchoring procedure may be applied to a variety of gastrectomies. For example, the anchoring procedure may be applied to the safe sleeve gastrectomy as disclosed in U.S. Pat. No. 10,016,295 as well as the safe sleeve gastrectomy with intestinal switch as disclosed in U.S. Pat. No. 10,238,519, both of which are incorporated herein by reference.

In addition, it will be understood that the anchoring procedure may be applied to tissues other than a sleeve 116 or stomach 104 during gastrectomies as well as other surgical procedures where immobilization is desired.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A method for a gastrectomy comprising:
dividing a stomach to form a sleeve;
accessing one or more portions of retroperitoneal fat; and
anchoring one or more portions of the sleeve to the one or more portions of the retroperitoneal fat with one or more bindings.

2. The method of claim 1, wherein the one or more portions of retroperitoneal fat are accessed through one or more portions of mesenteric fat.

3. The method of claim 1, wherein accessing the one or more portions of the retroperitoneal fat comprises making an incision in one or more portions of mesenteric fat.

4. The method of claim 1, further comprising positioning the one or more portions of the sleeve adjacent the one or more portions of the retroperitoneal fat prior to anchoring the one or more portions of the sleeve.

5. The method of claim 1, further comprising engaging the one or more portions of the sleeve with the one or more portions of the retroperitoneal fat prior to anchoring the one or more portions of the sleeve.

6. The method of claim 1, wherein the one or more bindings number no more than three bindings.

7. The method of claim 1, wherein the one or more portions of the sleeve are anchored such that an opening at an angularis of the sleeve is maintained.

8. A method for post gastrectomy anchoring of a sleeve created during a gastrectomy comprising:
   accessing one or more portions of retroperitoneal fat;
   positioning one or more portions of the retroperitoneal fat adjacent the sleeve; and
   anchoring the one or more portions of the retroperitoneal fat to one or more portions of the sleeve with one or more bindings;
   wherein the retroperitoneal fat is accessed through one or more portions of mesenteric fat.

9. The method of claim 8, wherein accessing the one or more portions of the retroperitoneal fat comprises making an incision in one or more portions of mesenteric fat.

10. The method of claim 8, wherein the one or more bindings number no more than three bindings.

11. The method of claim 8, wherein the one or more portions of the sleeve are anchored such that an opening at an angularis of the sleeve is maintained.

12. The method of claim 8, wherein the one or more portions of the sleeve are anchored to hold the sleeve in a bent shape.

13. The method of claim 8, wherein the sleeve comprises a greater curve and the one or more bindings are installed at the greater curve of the sleeve.

14. The method of claim 8, further comprising engaging the one or more portions of the retroperitoneal fat with the one or more portions of the sleeve.

15. A method for reducing post gastrectomy complications comprising:
   positioning one or more portions of a sleeve created during a gastrectomy relative to retroperitoneal fat; and
   anchoring the one or more portions of the sleeve to the retroperitoneal fat with one or more bindings;
   wherein the one or more bindings extend through one or more portions of mesenteric fat when anchoring the one or more portions of the sleeve to the retroperitoneal fat.

16. The method of claim 15, wherein the one or more bindings number no more than two bindings.

17. The method of claim 15, wherein the one or more bindings number no more than three bindings.

18. The method of claim 15, wherein the one or more portions of the sleeve are anchored such that an opening at an angularis of the sleeve is maintained.

19. The method of claim 15, wherein the one or more portions of the sleeve are anchored to hold the sleeve in a bent shape.

20. The method of claim 15, wherein the sleeve comprises a greater curve and the one or more bindings are installed at the greater curve of the sleeve.

\* \* \* \* \*